United States Patent [19] [11] 4,042,562
Hofer et al. [45] Aug. 16, 1977

[54] NITROGEN-CONTAINING AROMATIC HETEROCYCLIC COMPOUNDS AS ANTI-OXIDANTS

[75] Inventors: Kurt Hofer, Münchenstein; Guenther Tscheulin, Riehen, both of Switzerland

[73] Assignee: Sandoz Ltd., Basel, Switzerland

[21] Appl. No.: 620,535

[22] Filed: Oct. 6, 1975

Related U.S. Application Data

[63] Continuation-in-part of Ser. No. 415,368, Nov. 13, 1973, abandoned.

[30] Foreign Application Priority Data

Nov. 15, 1972 Switzerland .................... 16602/72

[51] Int. Cl.² ............... C08K 5/35; C07D 413/14; C07D 413/04
[52] U.S. Cl. ................ 260/45.8 NT; 544/208; 544/211; 544/198; 544/83; 544/113; 544/197; 544/209
[58] Field of Search ........ 260/249.6, 246 B, 45.8 NT, 260/246 B, 247.5 C

[56] References Cited

U.S. PATENT DOCUMENTS 3,869,423  3/1975  Minagawa et al. ............ 260/249.6
3,878,163  4/1975  Dexter et al. ................ 260/249.6

FOREIGN PATENT DOCUMENTS 1,507,062  11/1967  France

OTHER PUBLICATIONS

Thomae, Dr. Karl, G.m.b.H., Chemical Abstracts, vol. 70, 28,946g (1969).

*Primary Examiner*—Donald G. Daus
*Assistant Examiner*—Jose Tovar

*Attorney, Agent, or Firm*—Gerald D. Sharkin; Richard E. Vila; Joseph J. Borovian

[57] ABSTRACT

The present invention concerns novel nitrogen-containing aromatic heterocyclic compounds of the formula:

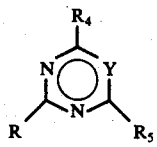

wherein R is a group of the formula

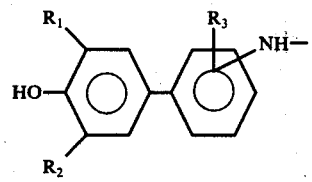

wherein $R_1$ and $R_2$ are substituents, e.g. alkyl and $R_3$ is hydrogen or a substituent, e.g. alkyl; $R_4$ is a group $R_{14}$ —X—, wherein $R_{14}$ is a substituent, e.g. alkyl and X is —O—, —S— or

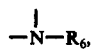

wherein $R_6$ is hydrogen or a substituent, e.g. alkyl, or $R_4$ is a heterocyclic ring or has one of the significances of R; $R_5$ has one of the significances of $R_4$; and Y is —N= or —CH=.

The compounds are useful as anti-oxidants in, e.g. plastics materials.

6 Claims, No Drawings

NITROGEN-CONTAINING AROMATIC HETEROCYCLIC COMPOUNDS AS ANTI-OXIDANTS

The present application is a continuation-in-part of our copending application Ser. No. 415,368, filed Nov. 13, 1973, now abandoned.

The present invention relates to heterocyclic compounds and more specifically to nitrogen-containing aromatic heterocyclic compounds suitable for use as anti-oxidants.

Accordingly, the present invention provides compound of formula I,

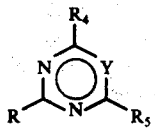

I wherein R is a group of the formula

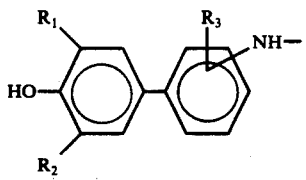

wherein $R_1$ is tertiary alkyl($C_4$–$C_9$), $R_2$ is alkyl($C_1$–$C_{18}$), cycloalkyl ($C_5$–$C_{12}$), cycloalkyl($C_5$–$C_{11}$)-alkyl($C_1$–$C_7$), alkyl($C_1$–$C_7$) cycloalkyl)$C_5$–$C_{11}$) alkyl($C_1$–$C_6$) cycloalkyl)$C_5$–$C_{10}$)alkyl($C_1$–$C_6$), aralkyl($C_7$–$C_{12}$) or alkyl($C_1$–$C_5$)-aralkyl($C_7$–$C_{11}$), and $R_3$ is hydrogen, alkyl($C_1$–$C_9$), cycloalkyl($C_5$–$C_9$), cycloalkyl($C_9$),cycloalkyl($C_5$–$C_8$)-alkyl($C_1$–$C_4$), alkyl($C_1$–$C_4$)cycloalkyl($C_5$–$C_8$), alkyl($C_1$–$C_3$)cycloalkyl($C_5$–$C_7$)alkyl($C_1$–$C_3$), halogen, —CN, —$CF_3$, a group

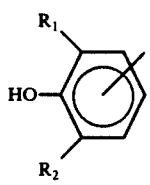

wherein $R_1$ and $R_2$ are as defined above, a group —CO.OM' wherein M' is hydrogen or cationic Ni, Zn, Mn or Ca, a group —CO.OZ wherein Z is alkyl($C_1$–$C_9$), or a group —CO—NHZ wherein Z is as defined above, $R_4$ is a group $R_{14}$—X—wherein $R_{14}$ is alkyl ($C_1$–$C_{18}$), cycloalkyl-($C_5$–$C_{12}$), cycloalkyl($C_5$–$C_{11}$)-alkyl ($C_1$–$C_7$), alkyl($C_1$–$C_7$)-cycloalkyl($C_5$–$C_{11}$), alkyl-($C_1$–$C_6$)cycloalkyl($C_5$–$C_{10}$)-alkyl($C_1$–$C_6$), aralkyl($C_7$–$C_{12}$), alkyl ($C_1$–$C_5$) aralkyl ($C_7$–$C_{11}$), phenyl, or aralkyl($C_7$–$C_{12}$) or phenyl substituted on the aryl nucleus by up to three of the substituents hydroxy, halogen, phenyl, benzyl, phenoxy, alkyl ($C_1$–$C_{12}$) and alkoxy ($C_1$–$C_{18}$) with the proviso that the maximum number of the substituents hydroxy, phenyl, benzyl and phenoxy is one, that the aggregate number of alkyl carbon atoms is 1-12 and that the aggregate number of alkoxy carbon atoms is 1-18, and X is —O—, —S— or

wherein $R_6$ is hydrogen, alkyl-($C_1$–$C_9$), cycloalkyl($C_5$–$C_9$), cycloalkyl($C_5$–$C_9$)-alkyl($C_1$–$C_4$), alkyl-($C_1$–$C_4$)cycloalkyl-($C_5$–$C_8$) or alkyl-($C_1$–$C_3$)cycloalkyl-C $_5$–$C_7$) alkyl ($C_1$–$C_3$), a heterocyclic ring

wherein A is a hydrocarbon (e.g. an alkylene) ($C_4$–$C_6$) chain, or a hydrocarbon (e.g. an alkylene) ($_3$–$C_5$) chain containing a hetero atom linkage, e.g. —O— or —N-H—, or has one of the significances of R, $R_5$ has one of the significances of $R_4$ and Y is —N= or —CH=.

It is to be understood that by the term "halogen" as used herein is meant fluorine, chlorine or bromine, preferably chlorine.

When any of $R_2$, $R_3$, $R_4$, $R_5$, $R_6$ or Z is, or includes, an akyl group, then unless otherwise indicated, the alkyl group may be linear or branched, primary, secondary or tertiary. Thus, examples of primary, secondary and tertiary alkyl groups contemplated, unless otherwise indicated, are the primary alkyl groups, methyl ethyl, n-propyl, n-butyl, n-pentyl and n-hexyl, the secondary alkyl groups isopropyl and 2-butyl and the tertiary alkyl groups tertiary butyl and 2-methyl-2-butyl.

Preferably $R_1$ is tertiary alkyl of 4 to 8, particularly 4, 5 or 6, especially 4, carbon atoms.

Preferably $R_2$ is alkyl of 1 to 18, more preferably 4 to 9, especially 4 to 6 carbon atoms, especially when branched, particularly tertiary alkyl, e.g. tert. butyl.

When $R_3$ is or includes alkyl, e.g. in the form of substituent Z, this preferably contains 1 to 6, more preferably 1 to 4, especially 1 to 3 carbon atoms.

When $R_{14}$ of $R_4$ or $R_5$ is alkyl, this preferably contains 1 to 12, more preferably 1 to 8, particularly 1 to 4 carbon atoms.

When any of $R_2$, $R_3$, $R_4$, $R_5$ or $R_6$ is or includes cycloalkyl, e.g. cycloalkylalkyl, then unless otherwise indicated examples are cyclopentyl, cyclohexyl, cycloheptyl and cyclododecyl. Preferably any such cycloalkyl significance contains 5, 6 or 7 carbon atoms and is more preferably cyclohexyl. Examples of cycloalkylalkyl groups are cyclohexylmethyl and 2-cyclohexylethyl.

When any of $R_2$, $R_4$ or $R_5$ is or includes aralkyl, this is preferably phenylalkyl such as benzyl and 2-phenylethyl.

Examples of particularly suitable significances of $R_3$ are hydrogen, chlorine, alkyl ($C_1$–$C_9$) 3,5-di-tert.-butyl-4-hydroxyphenyl, -CO.Oalkyl($C_1$–$C_3$), especially hydrogen.

Examples of particularly suitable significances of $R_{14}$ are alkyl ($C_1$–$C_{12}$), benzyl, chorobenzyl, phenyl, 4-tert.-butylphenyl, 2-, 3- or 4- alkyl($C_1$–$C_3$) phenyl, or diphenyl, especially methyl, dodecyl, 4-tert.butylphenyl or phenyl.

X is preferably —O—, —S— or —NH—.

Y is preferably —N=.

A preferred group of compounds are the compounds of formula Ia,

Ia

-continued

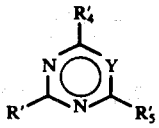

wherein R' is a group of the formula

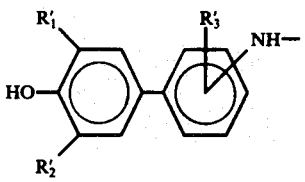

wherein $R_1'$ is tertiary alkyl ($C_4$-$C_6$), $R_2'$ is alkyl ($C_4$-$C_9$), $R_3'$ is hydrogen, halogen, alkyl($C_1$-$C_9$), a group

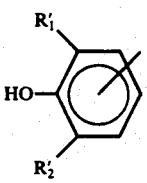

wherein $R_1'$ and $R_2'$ are as defined above or a group —CO.OZ' wherein Z' is alkyl($C_1$-$C_4$), $R_4'$ is a group $R_{14}'$—X'—
wherein $R_{14}'$ is alkyl($C_1$-$C_{18}$), phenyl, benzyl, or phenyl or benzyl substituted on the phenyl nucleus by up to three of the substituents alkyl($C_1$-$C_{12}$) and alkoxy($C_1$-$C_{18}$) with the proviso that the maximum number of each of the substituents alkyl and alkoxy is two, that the aggregate number of alkyl carbon atoms is 1-12 and that the aggregate number of alkoxy carbon atoms is 1-18, and X' is —O—, —S— or

wherein $R_6'$ is hydrogen or alkyl($C_1$-$C_9$), or a heterocyclic ring

wherein A' is a hyrocarbon ($C_4$-$C_5$) chain or a hydrocarbon ($C_3$-$C_4$) chain containing one —O— or —NH— linkage, preferably piperidino, morpholino or pyrrolidino, and $R_5'$ has one of the significances of R' or $R_4'$ and Y is as defined above, with the proviso that the —NH— function of any group R' is in a position ortho or para to the diphenyl bond.

A further preferred group of compounds are the compounds of formula Ib,

Ib

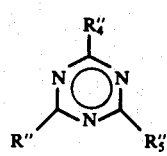

wherein R" is a group of the formula

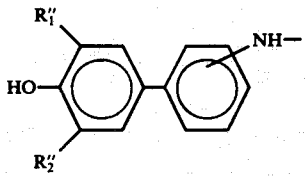

wherein $R_1''$ and $R_2''$ are each tert-butyl, $R_4''$ is a group $R_{14}''$—X"
wherein $R_{14}''$ is alkyl($C_1$-$C_{12}$), benzyl, phenyl, or benzyl or phenyl mono substituted on the phenyl nucleus by alkyl($C_1$-$C_4$) or alkoxy($C_1$-$C_4$) and X" is —O—, —S— or —NH—, or piperidino, morpholino or pyrrolidino, and $R_5''$ has one of the significances of R" or $R_4''$, with the proviso that the —NH— function of any group R" is in a position ortho or para to the diphenyl bond.

A further preferred group of compounds are the compound of formula Ic,

Ic

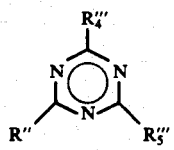

wherein R" is as defined above,
$R_4'''$ is a group $R_{14}'''$—X'''— wherein $R_{14}'''$ is alkyl ($C_1$-$C_4$), phenyl or phenyl mono substituted by alkyl ($C_1$-$C_4$), and X''' is —O— or —S—, or a morpholino group and
$R_5'''$ has one of the significances of R" or $R_4''$ with the provisio that the —NH— function of any group R" is in a position ortho or para to the diphenyl bond.

The present invention also provides a process for the production of a compound of formula I which comprises a. condensing a compound of formula II,

II

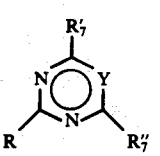

wherein R and Y are as defined above and each of
$R_7'$ and $R_7''$ is halogen or $R_4$ wherein $R_4$ is as defined above at least one of $R_7'$ and $R_7''$ being halogen, with a compound of formula III, $R_4M''$ III wherein $R_4$ is as defined above and
M" is hydrogen, or an alkali metal or an ammonium cation, to produce a compound of formula I'

I'

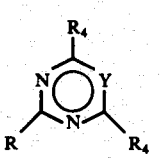

wherein Y, R and R₄ are as defined above, or
b. condensing a compound of formula IV,

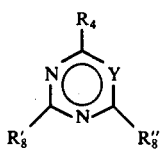
IV wherein R₄ and Y are as defined above and each of R₈'
and R₈" is halogen or R wherein R is as defined above
at least one of R₈' and R₈" being halogen, with a compound of formula V,

RH    V wherein R is as defined above, to obtain a compound of formula I",

I"

wherein Y, R and R₄ are as defined above.

The process in accordance with variant a) may, for example, be effected as follows The compound of formula II is conveniently reacted with the compound of formula III in a solvent such as an alcohol, e.g. methanol or ethanol. The reaction is preferably effected in an inert atmosphere such as a nitrogen atmosphere. The reaction is conveniently effected at a elevated temperature, e.g. at the boiling temperature of the reaction mixture under reflux. The compounds are preferably employed in a molar ratio of 1 mole of the compound of formula II: n moles of the compound of formula III, wherein n represents the number of halogen substituents on the aromatic heterocyclic nucleus of the compound of formula II [For description of analogous process, see JACS 73, 2986(1951)].

When M" of formula III is hydrogen then the reaction is preferably effected in the presence of an acid acceptor such as an amine, e.g. triethylamine, an alkali metal hydroxide, carbonate or bicarbonate, e.g. sodium hydroxide, sodium carbonate or sodium bicarbonate, or pyridine. Preferably however, M is an alkali metal, particularly sodium or potassium, or ammonium.

Working up is effected in conventional manner.

The process in accordance with process variant b) may, for example, be effected as follows.

The compound of formula IV is conveniently reacted with the compound of formula V in a solvent such as a ketone, e.g. acetone. The reaction is preferably effected at a temperature below room temperature, e.g. between 0° and 10° C. The reaction is suitably effected in the presence of an acid acceptor, e.g. an amine such as triethylamine, an alkali metal hydroxide, carbonate or bicarbonate such as sodium hydroxide, sodium carbonate or sodium bicarbonate or pyridine. The compounds are preferably employed in a molar ratio of 1 mole of the compound of formula IV : n moles of the compound of formula V, wherein n represents the number of halogen substituents on the aromatic heterocyclic nucleus of the compound of formula IV.

The compounds of formula II employed as starting material in process variant a) above, may be produced by condensing a compound of formula VI,

VI wherein Y, R₇' and R₇" are as defined above and Hal is halogen, with a compound of formula V.

The process for the production of a compound of formula II, may be effected in analogous manner to that described above in relation to process variant b).

The compounds of formula II are new and also form part of the present invention.

The compounds of formula IV, employed as starting material in process variant b) above, may be produced by condensing a compound of formula VII,

VII wherein Y, R₈', R₈" and Hal are as defined above, with a compound of formula III.

The process for the production of a compound of formula IV, may be effected in analogous manner to that described above in relation to process variant a).

The compounds of formula I, possess antioxidant properties, i.e. they protect sensitive organic material from degradation under the effect of oxidation as indicated in the following tests 1 and 2 below, viz.

Polypropylene powder is intimately mixed with 0.4% by weight of the test compound and the mixture kneaded on a roller mill at 180° C for 5 minutes. The kneaded mixture is then pressed into discs of 18 mm diameter and 1 mm thickness. The plastic discs so produced and incorporating the test compounds are employed in Tests 1 and 2.

Test 1: The polypropylene discs incorporating the test compounds, e.g. the compound of formula are stored in an hermetically sealed chamber having an oxygen atmosphere, at a temperature of 190° C and an initial excess pressure of 200 mm Hg. The temperature of each polypropylene disc is kept constant, the excess pressure of oxygen, which falls with oxidation of the polymer, being monitored. The period, in minutes, for the excess oxygen pressure to be reduced to zero is measured.

The results are compared with an unstabilized control disc tested under the same conditions. A fall in pressure in the case of the stabilized discs which is slower in rate than that in the case of the unstabilized disc indicates an anti-oxidant effect of the test compound.

Test 2: The polypropylene discs incorporating the test compounds, e.g. the compound of formula

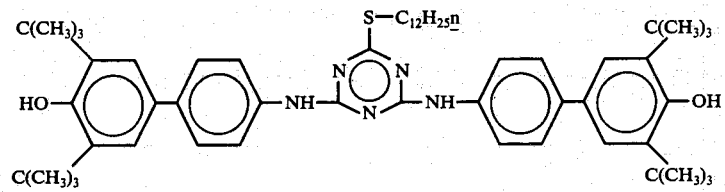

are stored in a hot air oven at a constant temperature of 140° C and the time in hours is measured for a distinct change in the physical appearance of each disc to occur, e.g. surface cracking, blooming or colour change.

The times recorded in the case of the stabilized discs are compared with the time recorded for an unstabilized disc. A longer time in the case of the stabilized disc indicates an anti-oxidant effect of the test compound.

The compound of formula I are therefore useul in the stabilization of organic material, particularly plastics material, susceptible to oxidation, by a method which comprises treating the organic material with a compound of formula I.

It is to be understood that by the term "treating" is meant either surface coating the organic material with the compound of formula I, in the form of a film, or incorporating the compound of formula I into the body of the organic material, preferably the latter, in manner known per se.

The above method also forms part of the present invention.

According to a first embodiment, of the method of the invention the anti-oxidant is intimately mixed with a particulate form of, for example, a plastics material, such as polypropylene, e.g. polypropylene granules, in a kneader or other suitable device, to obtain uniform distribution of the anti-oxidant throughout the plastics material. The plastics material may thereafter be formed into final shape, e.g. by extrusion or injection moulding. By such method, uniform distribution of the anti-oxidant throughout the body of the final material is achieved which is important for good protection.

According to a second embodiment of the method of the present invention, particularly suited to stabilization of polymers or copolymers susceptible to degradation by oxidation, e.g. polypropylene, the antioxidant is mixed with the monomer or prepolymer before polymerisation is effected, to yield the polymer or copolymer having the anti-oxidant uniformly distributed therethrough. The polymer or copolymer may thereafter be extruded, moulded or otherwise formed into final shape.

Examples of organic materials susceptible to oxidation and embraced by the method of the present invention are cellulose derivatives, e.g. cellulose acetate, cellulose acetobutyrate, ethyl cellulose, cellulose nitrate and cellulose propionate, polyalkylenes, e.g. polyethylene and polypropylene, polyvinyl derivatives, e.g. polyvinyl chloride, polyvinyl chloride acetate and polyvinyl alcohol, polyamides, polyesters, polyacrylonitrile, polystyrene, silicon rubber, melamineformaldehyde resins, resins, urea-formaldehyde resins, allyl casting resins, polymethylmethacrylate, copolymers such as acrylonitrile — butadiene — styrene copolymers and natural products such as rubber, cellulose, wool and silk.

Stabilized organic materials according to the invention may exist in solid form, e.g. solid foams such as foam plastics, rods, coatings, sheets such as paper, films, tapes, fibres, granules or powders, or in liquid form, e.g. solutions, emulsions or dispersions such as polishes, paints and creams.

The organic material may also be treated with other additives, e.g. heat and u.v. stabilizers. Other additives that may be mentioned are 2-hydroxybenzophenones, organic sulphur compounds, tin and trivalent phosphorus compounds and nickel salts of carboxylic acids.

The amount of anti-oxidant employed in the method of the present invention will of course vary with the mode of application, the compound employed and the nature of the organic material to be treated.

Thus, for example, when the mode of application is the uniform distribution of the anti-oxidant throughout the body of the organic material, then in general, satisfactory results are obtained when the amount of anti-oxidant employed is between 0.01 and 5%, preferably between 0.05 and 1% of the weight of organic material to be treated.

Examples of the process of the invention will now be described. Where temperatures are referred to, these are in °C. Where parts and percentages are referred to, these are by weight.

EXAMPLE 1 a. A hot solution of 9.2 parts cyanurochloride and 40 parts acetone is added dropwise to 100 parts ice-water at 0°-5° C which results in the formation of a white precipitate. After 14.8 parts 3,5-di-tert.-butyl-4-hydroxy-4′-aminobiphenyl and 2.7 parts soda are added portionwise, stirring is continued for 1 hour at 6°-10° C. After subsequent dilution with 40 parts acetone and reaction for another hour at the same temperature the suspension is poured into icewater, the precipitate filtered with suction, washed twice with 100 parts icewater and dried under vacuum. A light-yellow powder is obtained which may be further reacted without additional purification and which has a melting range of 175°-185° C. It is of formula temperature, about 100 parts water are added slowly dropwise, the precipitate is filtered off and recrystallized from alcohol/water. The compound of formula

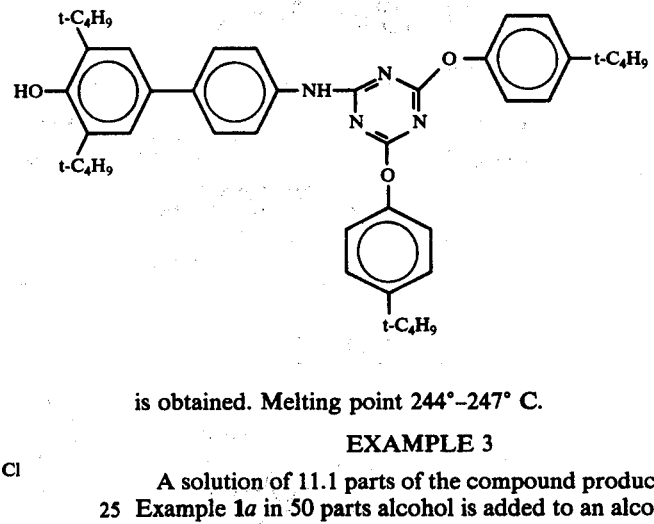

is obtained. Melting point 244°-247° C.

EXAMPLE 3

A solution of 11.1 parts of the compound produced in Example 1a in 50 parts alcohol is added to an alcoholic solution of sodium dodecyl-mercaptate (produced from 10.1 parts dodecylmercaptan, 2.7 parts sodium methylate in 50 parts alcohol) and boiled for 2 hours in a mild current of nitrogen gas with reflux. The solution is subsequently evaporated under vacuum, the oily residue dissolved in toluene and the organic phase washed several times in water. On drying over $MgSO_4$ the toluene solution is evaporated under vacuum. The oily residue is crystallized from methanol. The compound of formula

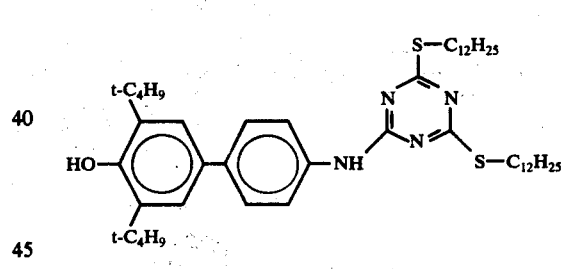

is obtained.

The compounds of Examples 4 – 10 are produced by analogy with the procedure of Examples 1-3 employing appropriate amounts of the corresponding starting materials.

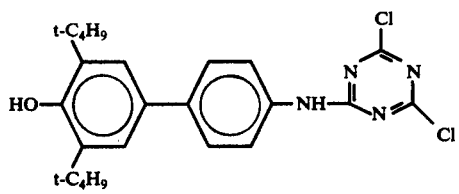

b. 2.92 Parts sodium methylate are added portionwise to a solution of 12 parts of the compound produced in Example 1a and 50 parts methanol and boiled for 3 hours in a mild current of nitrogen gas with reflux. On cooling to room temperature, about 100 parts water are added slowly dropwise, the precipitate is filtered off and recrystallized from methanol/water. The compound of formula

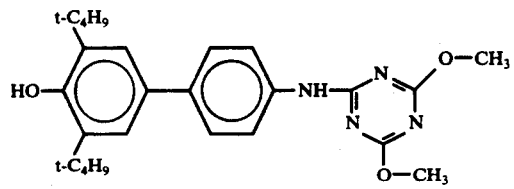

is obtained. Melting point 203°-205° C.

EXAMPLE 2

A solution of 8.9 parts of the compound produced in Example 1a in alcohol is added to an alcoholic solution of sodium-4-tert.-butylphenolate (produced from 2.1 parts sodium methylate and 6 parts 4-tert.-butylphenol, and boiled for 2 hours with reflux. On cooling to room

TABLE I

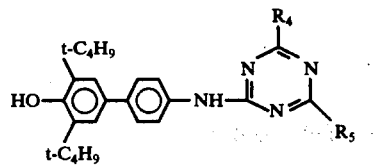

| Example No. | $R_4$ | $R_5$ | M. pt. |
|---|---|---|---|
| 4 | —O—⟨Ph⟩ | —O—⟨Ph⟩ | 182 – 183° |
| 5 | —S—⟨Ph⟩—C(CH₃)₃ | —S—⟨Ph⟩—C(CH₃)₃ | 176 – 180° |

TABLE I-continued

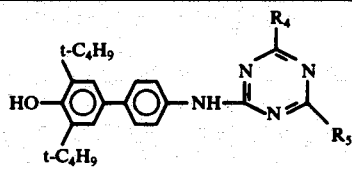

| Example No. | R₄ | R₅ | M. pt. |
|---|---|---|---|
| 6 | —S—C₁₂H₂₅(n) | (structure: —NH—C₆H₄—C₆H₂(C(CH₃)₃)₂OH) | 170 – 173° |

TABLE II

| Ex. No. | | M. pt. |
|---|---|---|
| 7 | (morpholine-triazine-biphenyl-OH structure) | 143–145° |
| 8 | (bis-triazine tri-phenol structure) | 247–246° |
| 9 | (bis-dodecylamino triazine structure) | — |
| 10 | (bis-triazine biphenyl structure) | — |

What is claimed is:

1. A compound of the formula

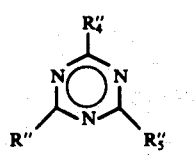

wherein R″ is a group of the formula

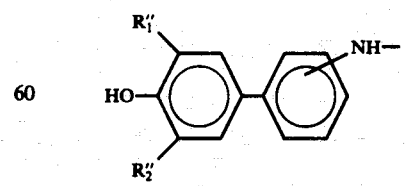

wherein $R_1''$ and $R_2''$ are each tert.butyl,
$R_4''$ is piperidino, morpholino or pyrrolidino, or has one of the significances of R″, and
$R_5''$ has one of the significances of $R_4''$, with the proviso that the —NH— function of any group R" is in a position ortho or para to the diphenyl bond.

2. A compound of claim 1 of the formula:

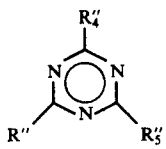

wherein
R" is as defined in claim 1,
R₄" is piperidino, morpholino or pyrrolidino, and
R₅" has one of the significances of R" or R₄",
with the proviso that the —NH— function of any group R" is in a position ortho or para to the diphenyl bond.

3. A compound of claim 2 of the formula:

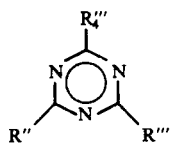

wherein
R" is as defined in claim 2,
R₄'" is morpholino, and
R₅'" has one of the significances of R" or R₄'", with the proviso that the —NH— function of any group R" is in a position ortho or para to the diphenyl bond.

4. A compound of claim 3, of the formula:

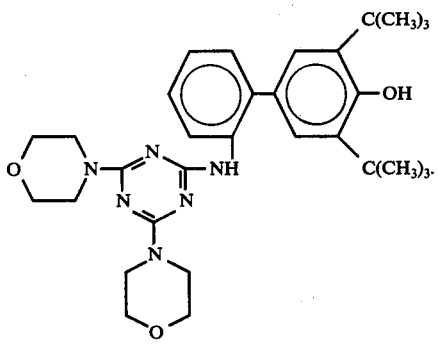

5. A method of stabilizing a natural or synthetic polymeric material susceptible to oxidation which comprises treating said material with a compound of claim 1, in sufficient amount to impart an anti-oxidant effect.

6. Natural or synthetic polymeric material treated with a compound of claim 1 as anti-oxidant.

* * * * *